(12) United States Patent
Jin et al.

(10) Patent No.: US 11,026,657 B2
(45) Date of Patent: Jun. 8, 2021

(54) ULTRASOUND DIAGNOSIS APPARATUS AND METHOD OF OPERATING THE SAME

(71) Applicant: SAMSUNG MEDISON CO., LTD., Hongcheon-gun (KR)

(72) Inventors: Gil-ju Jin, Hongcheon-gun (KR); Jae-moon Jo, Hongcheon-gun (KR); Yu-ri Kim, Hongcheon-gun (KR); Mi-jeoung Ahn, Hongcheon-gun (KR)

(73) Assignee: SAMSUNG MEDISON CO., LTD., Hongcheon-gun (KR)

( * ) Notice: Subject to any disclaimer, the term of this patent is extended or adjusted under 35 U.S.C. 154(b) by 496 days.

(21) Appl. No.: 15/871,261

(22) Filed: Jan. 15, 2018

(65) Prior Publication Data

US 2019/0059856 A1 Feb. 28, 2019

Related U.S. Application Data

(60) Provisional application No. 62/550,124, filed on Aug. 25, 2017.

(30) Foreign Application Priority Data

Dec. 27, 2017 (KR) .................... 10-2017-0181452

(51) Int. Cl.
*A61B 8/00* (2006.01)
*A61B 8/08* (2006.01)

(52) U.S. Cl.
CPC .......... *A61B 8/4472* (2013.01); *A61B 8/4438* (2013.01); *A61B 8/465* (2013.01);
(Continued)

(58) Field of Classification Search
CPC .................................................. A61B 8/4472
See application file for complete search history.

(56) References Cited

U.S. PATENT DOCUMENTS 9,610,065 B2 4/2017 Kim et al.
9,622,718 B2 4/2017 Watanabe
(Continued)

FOREIGN PATENT DOCUMENTS

JP 2008-000406 A 1/2008
JP 5519949 B2 6/2014
(Continued)

OTHER PUBLICATIONS

International Search Report and Written Opinion (PCT/ISA/210 and PCT/ISA/237), dated Aug. 8, 2018 by International Searching Authority in International Application No. PCT/KR2018/004276.
(Continued)

*Primary Examiner* — Joseph M Santos Rodriguez
(74) *Attorney, Agent, or Firm* — Sughrue Mion, PLLC

(57) ABSTRACT

Provided is an ultrasound diagnosis apparatus connected with at least one wired ultrasound probe and at least one wireless ultrasound probe. The ultrasound diagnosis apparatus includes: at least one wired ultrasound probe connected via wire to the ultrasound diagnosis apparatus; at least one wireless ultrasound probe connected to the ultrasound diagnosis apparatus by using wireless communication; a wireless communication module configured to receive a pairing reception signal from the at least one wireless ultrasound probe to thereby be connected with the at least one wireless ultrasound probe by using a wireless communication method and to transmit and receive a beamforming control signal and ultrasound image data to and from each of the at least one wireless ultrasound probe; and a controller configured to detect an ultrasound probe being used by a user, and activate the detected ultrasound probe.

28 Claims, 9 Drawing Sheets

(52) U.S. Cl.
CPC ............... *A61B 8/5207* (2013.01); *A61B 8/54* (2013.01); *A61B 8/56* (2013.01)

(56) References Cited

U.S. PATENT DOCUMENTS

| | | | |
|---|---|---|---|
| 2007/0106143 A1 | 5/2007 | Flaherty | |
| 2008/0300489 A1 | 12/2008 | Schutz et al. | |
| 2010/0249600 A1* | 9/2010 | Kudoh | A61B 8/06 600/459 |
| 2011/0105904 A1* | 5/2011 | Watanabe | A61B 8/00 600/443 |
| 2012/0101389 A1 | 4/2012 | Tanabe | |
| 2012/0232391 A1* | 9/2012 | Kojima | A61B 8/4477 600/443 |
| 2013/0028153 A1* | 1/2013 | Kim | H04W 84/12 370/310 |
| 2014/0323869 A1* | 10/2014 | Jin | A61B 8/565 600/459 |
| 2015/0238071 A1 | 8/2015 | Hua et al. | |
| 2018/0153519 A1 | 6/2018 | Cho et al. | |

FOREIGN PATENT DOCUMENTS

| | | |
|---|---|---|
| JP | 2014-521435 A | 8/2014 |
| KR | 10-2015-0027010 A | 3/2015 |
| KR | 10-1625661 B1 | 5/2016 |
| KR | 10-1733731 B1 | 5/2017 |
| WO | 2017/009735 A1 | 1/2017 |

OTHER PUBLICATIONS

Communication dated Mar. 29, 2021 issued by the European Patent Office in application No. 18847971.1.

* cited by examiner

ULTRASOUND DIAGNOSIS APPARATUS AND METHOD OF OPERATING THE SAME

CROSS-REFERENCE TO RELATED APPLICATIONS

This application claims the benefit of U.S. Provisional Application No. 62/550,124, filed on Aug. 25, 2017, in the US Patent Office and Korean Patent Application No. 10-2017-0181452, filed on Dec. 27, 2017, in the Korean Intellectual Property Office, the disclosures of which are incorporated herein in their entirety by reference.

BACKGROUND

1. Field

The present disclosure relates to ultrasound diagnosis apparatuses and methods of operating the same, and more particularly, to an ultrasound diagnosis apparatus including at least one wired ultrasound probe and a plurality of wireless ultrasound probes and a method of operating the ultrasound diagnosis apparatus.

2. Description of Related Art

Ultrasound systems transmit ultrasound signals generated by transducers of an ultrasound probe to an internal part of an object and receive information about echo signals reflected therefrom, thereby obtaining an image of the internal part of the object. In particular, ultrasound systems are used for medical purposes including observation of an internal area of an object, detection of foreign substances, diagnosis of damage to the object, and imaging of characteristics.

Wireless ultrasound probes connected to an ultrasound diagnosis apparatus by using wireless communication are nowadays being developed in order to improve the operability of an ultrasound probe by removing a communication cable for transmitting and receiving ultrasound image data between the ultrasound probe and the ultrasound diagnosis apparatus and eliminating the inconvenience caused by the communication cable. However, at the present time, an ultrasound diagnosis apparatus including a wireless ultrasound probe may contain only one wireless ultrasound probe, and only one wireless ultrasound probe may be connected to the ultrasound diagnosis apparatus at a time. Furthermore, in the case of an ultrasound diagnosis apparatus including both wired and wireless ultrasound probes, when a user stops using the wired ultrasound probe and attempts to use the wireless ultrasound probe, the user suffers the inconvenience of having to manually pair the wireless ultrasound probe to the ultrasound diagnosis apparatus and activate the paired wireless ultrasound probe.

SUMMARY

Provided are ultrasound diagnosis apparatuses including at least one wired ultrasound probe and at least one wireless ultrasound probe and configured to detect an ultrasound probe being used by a user, from among the at least one wired ultrasound probe and the at least one wireless ultrasound probe, and activate the detected ultrasound probe. Provided are also ultrasound diagnosis apparatuses for activating a wireless ultrasound probe being used among at least one wireless ultrasound probe paired using a wireless communication method.

Additional aspects will be set forth in part in the description which follows and, in part, will be apparent from the description, or may be learned by practice of the presented embodiments.

In accordance with an aspect of the present disclosure, an ultrasound diagnosis apparatus includes: at least one wired ultrasound probe connected via wire to the ultrasound diagnosis apparatus; at least one wireless ultrasound probe connected to the ultrasound diagnosis apparatus by using wireless communication; a wireless communication module configured to receive a pairing reception signal from the at least one wireless ultrasound probe to thereby be connected with the at least one wireless ultrasound probe by using a wireless communication method and to transmit and receive a beamforming control signal and ultrasound image data to and from each of the at least one wireless ultrasound probe; and a controller configured to detect an ultrasound probe being used by a user to examine an object, from among the at least one wired ultrasound probe and the at least one wireless ultrasound probe, and activate the detected ultrasound probe.

The ultrasound diagnosis apparatus may further include: a beamformer configured to generate a beamforming signal to be applied to each of a plurality of transducers included in each of at least one wired ultrasound probe, based on a position and a focal point of the plurality of transducers; and a probe switching assembly configured to select a wired ultrasound probe from among the at least one wired ultrasound probe and activate the selected wired ultrasound probe.

The controller may be further configured to detect a first wired ultrasound probe being used from among the at least one wired ultrasound probe, control the probe switching assembly to activate the detected first wired ultrasound probe, and control the beamformer to transmit the beamforming signal to the first wired ultrasound probe.

The controller may be further configured to stop operations of the beamformer and the probe switching assembly when the ultrasound probe detected as being used is switched from the wired ultrasound probe activated among the at least one wired ultrasound probe to one of the at least one wireless ultrasound probe.

The controller may be further configured to resume, when the ultrasound probe detected as being used is switched from the wireless ultrasound probe to the first wired ultrasound probe, the operations of the beamformer and the probe switching assembly, control the probe switching assembly to activate the first wired ultrasound probe, and control the beamformer to transmit the beamforming signal to the first wired ultrasound probe.

The controller may be further configured to control the wireless communication module to transmit, when the ultrasound probe detected as being used is a first wireless ultrasound probe, a beamforming control signal for controlling a beamformer included in the first wireless ultrasound probe to the first wireless ultrasound probe.

The controller may be further configured to control the wireless communication module to receive, from the at least one wireless ultrasound probe, status information including at least one of identification information, a wireless communication frequency, a connection type, an executable application, a wireless communication method, battery charging information, a remaining battery capacity, a remaining usability time, and a communication status with respect to each of the at least one wireless ultrasound probe.

The wireless communication module may be connected with the at least one wireless ultrasound probe by using at least one of wireless communication methods comprising a Wireless Local Area Network (WLAN), wireless fidelity (Wi-Fi), Bluetooth, Zigbee, Wi-Fi Direct (WFD), Infrared Data Association (IrDA), Bluetooth Low Energy (BLE), Near Field Communication (NFC), Wireless Broadband Internet (WiBro), World Interoperability for Microwave Access (WiMAX), Shared Wireless Access Protocol (SWAP), Wireless Gigabit Alliance (WiGig), and radio frequency (RF) communication.

The wireless communication module may be simultaneously paired with the at least one wireless ultrasound probe.

The controller may be further configured to check a status of wireless connection between the ultrasound diagnosis apparatus and the at least one wireless ultrasound probe at preset time intervals.

In accordance with another aspect of the present disclosure, an ultrasound diagnosis apparatus includes: a wireless communication module connected with each of a plurality of different wireless ultrasound probes by using a wireless communication method; and a controller configured to detect a wireless ultrasound probe being used by a user, from among the plurality of wireless ultrasound probes, and control the wireless communication module to transmit an activation signal to the detected wireless ultrasound probe.

The controller may be further configured to control the wireless communication module to transmit and receive a pairing signal to and from each of the plurality of wireless ultrasound probes by using a wireless communication method.

The controller may be further configured to control the wireless communication module to receive, from the plurality of wireless ultrasound probes, status information including at least one of identification information, a wireless communication frequency, a connection type, an executable application, a wireless communication method, battery charging information, a remaining battery capacity, a remaining usability time, and a communication status with respect to each of the plurality of wireless ultrasound probes.

The controller may be further configured to control the wireless communication module to transmit, to the wireless ultrasound probe, a beamforming control signal for controlling a beamformer included in the wireless ultrasound probe detected as being used.

The wireless communication module may be simultaneously paired with the plurality of wireless ultrasound probes.

In accordance with another aspect of the present disclosure, a method of operating an ultrasound diagnosis apparatus includes: connecting the ultrasound diagnosis apparatus with the at least one wireless ultrasound probe by using a wireless communication method; detecting an ultrasound probe being used by a user to examine an object, from among the at least one wired ultrasound probe and the at least one wireless ultrasound probe; and activating the detected ultrasound probe.

The activating of the detected ultrasound probe may include: detecting a first wired ultrasound probe being used, from among the at least one wired ultrasound probe; controlling a probe switching assembly included in the ultrasound diagnosis apparatus to activate the first wired ultrasound probe; and transmitting a beamforming signal to the first wired ultrasound probe.

The method may further include stopping an operation of the probe switching assembly and transmission of the beamforming signal when the ultrasound probe detected as being used is switched from the first wired ultrasound probe to one of the at least one wireless ultrasound probe.

The method may further include: resuming, when the ultrasound probe detected as being used is switched from the wireless ultrasound probe to a second wired ultrasound probe, the operation of the probe switching assembly to activate the second wired ultrasound probe; and transmitting the beamforming signal to the second wired ultrasound probe.

The activating of the detected ultrasound probe may include: detecting a first wireless ultrasound probe being used, from among the at least one wireless ultrasound probe; and transmitting a beamforming control signal for controlling a beamformer included in the first wireless ultrasound probe to the first wireless ultrasound probe.

The method may further include, after the connecting of the at least one wireless ultrasound probe with the ultrasound diagnosis apparatus, receiving, from the at least one wireless ultrasound probe, status information including at least one of identification information, a wireless communication frequency, a connection type, an executable application, a wireless communication method, battery charging information, a remaining battery capacity, a remaining usability time, and a communication status with respect to each of the at least one wireless ultrasound probe.

The connecting of the at least one wireless ultrasound probe with the ultrasound diagnosis apparatus may include connecting with the at least one wireless ultrasound probe by using at least one of wireless communication methods including a Wireless Local Area Network (WLAN), wireless fidelity (Wi-Fi), Bluetooth, Zigbee, Wi-Fi Direct (WFD), Infrared Data Association (IrDA), Bluetooth Low Energy (BLE), Near Field Communication (NFC), Wireless Broadband Internet (WiBro), World Interoperability for Microwave Access (WiMAX), Shared Wireless Access Protocol (SWAP), Wireless Gigabit Alliance (WiGig), and radio frequency (RF) communication.

The connecting of the at least one wireless ultrasound probe with the ultrasound diagnosis apparatus may include simultaneously pairing the ultrasound diagnosis apparatus with the at least one wireless ultrasound probe.

The connecting of the at least one wireless ultrasound probe with the ultrasound diagnosis apparatus may include checking a status of wireless connection between the ultrasound diagnosis apparatus and the at least one wireless ultrasound probe at preset time intervals.

In accordance with another aspect of the present disclosure, a method of operating an ultrasound diagnosis apparatus includes: connecting the ultrasound diagnosis apparatus with each of the plurality of wireless ultrasound probes by using a wireless communication method; detecting a wireless ultrasound probe being used by a user, from among the plurality of wireless ultrasound probes; and transmitting an activation signal to the detected wireless ultrasound probe.

The connecting of the plurality of wireless ultrasound probes with the ultrasound diagnosis apparatus may further include transmitting and receiving a pairing signal to and from each of the plurality of wireless ultrasound probes by using a wireless communication method.

The method may further include, after the connecting of the plurality of wireless ultrasound probes with the ultrasound diagnosis apparatus, receiving, from the plurality of wireless ultrasound probes, status information including at least one of identification information, a wireless communication frequency, a connection type, an executable application, a wireless communication method, battery charging information, a remaining battery capacity, a remaining usability time, and a communication status with respect to each of the plurality of wireless ultrasound probes.

The transmitting of the activation signal may include transmitting, to the wireless ultrasound probe, a beamforming control signal for controlling a beamformer included in the wireless ultrasound probe detected as being used.

The connecting of the plurality of wireless ultrasound probes with the ultrasound diagnosis apparatus may include simultaneously pairing the ultrasound diagnosis apparatus with the at least one wireless ultrasound probe.

In accordance with another aspect of the present disclosure, a computer- readable recording medium having recorded thereon a computer program including instructions for performing operations of: connecting the ultrasound diagnosis apparatus with the wireless ultrasound probes by using a wireless communication method; detecting an ultrasound probe being used by a user to examine an object, from among the at least one wired ultrasound probe and the wireless ultrasound probes; and activating the detected ultrasound probe.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
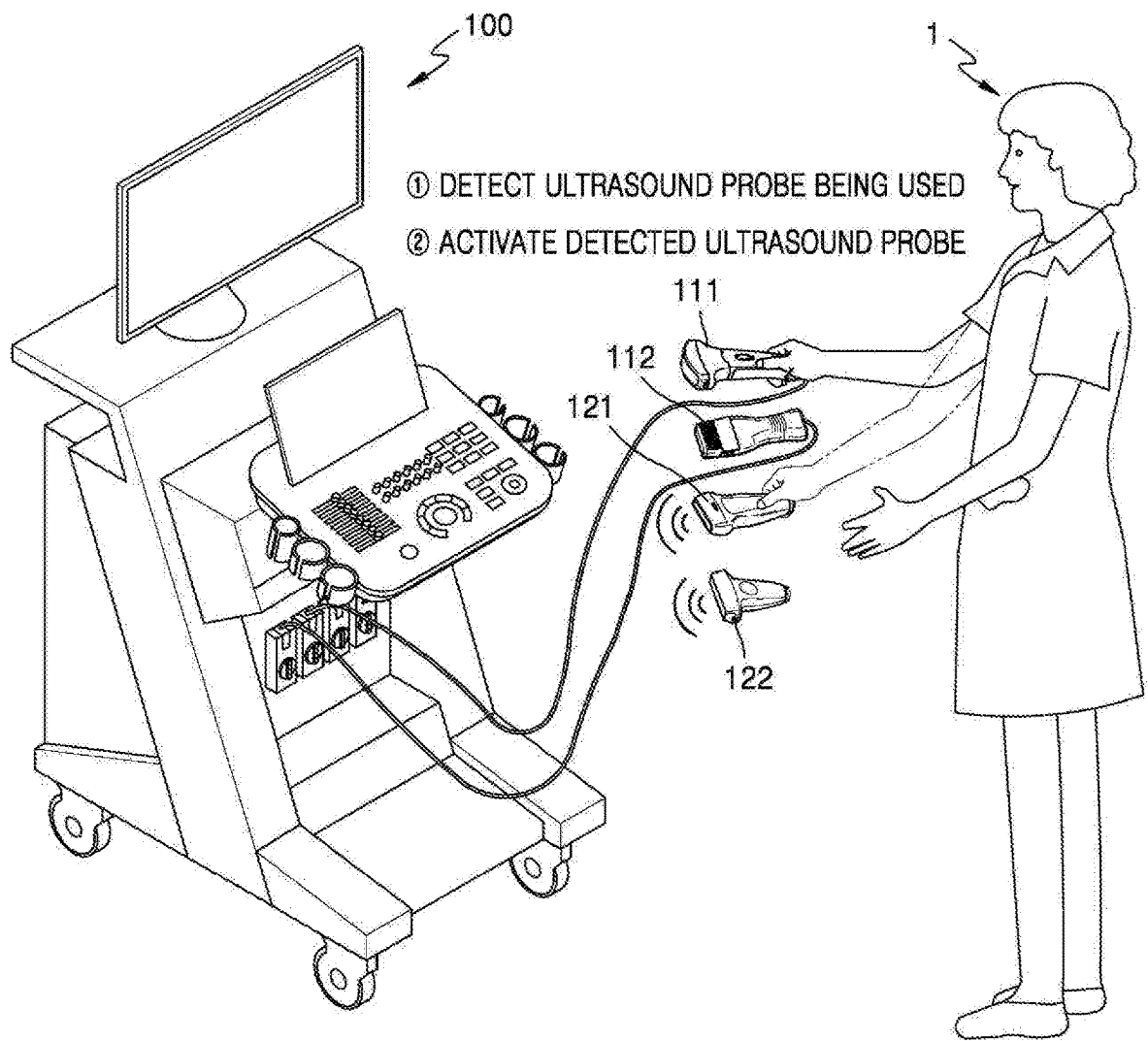
FIG. 1 is a conceptual diagram illustrating an example in which an ultrasound diagnosis apparatus detects an ultrasound probe being used by a user, from among wired and wireless ultrasound probes, and activates the detected ultrasound probe, according to an embodiment.

Advantages and features of one or more embodiments of the present disclosure and methods of accomplishing the same may be understood more readily by reference to the following detailed description of the embodiments and the accompanying drawings. In this regard, the present embodiments may have different forms and should not be construed as being limited to the descriptions set forth herein. Rather, these embodiments are provided so that this disclosure will be thorough and complete and will fully convey the concept of the present embodiments to one of ordinary skill in the art, and the present disclosure will only be defined by the appended claims.

Terms used herein will now be briefly described and then one or more embodiments of the present disclosure will be described in detail.

All terms including descriptive or technical terms which are used herein should be construed as having meanings that are obvious to one of ordinary skill in the art. However, the terms may have different meanings according to the intention of one of ordinary skill in the art, precedent cases, or the appearance of new technologies. Also, some terms may be arbitrarily selected by the applicant, and in this case, the meaning of the selected terms will be described in detail in the detailed description of the disclosure. Thus, the terms used herein have to be defined based on the meaning of the terms together with the description throughout the specification.

When a part "includes" or "comprises" an element, unless there is a particular description contrary thereto, the part can further include other elements, not excluding the other elements. Also, the term "unit" in the embodiments of the present disclosure means a software component or hardware component such as a field-programmable gate array (FPGA) or an application-specific integrated circuit (ASIC), and performs a specific function. However, the term "unit" is not limited to software or hardware. The "unit" may be formed so as to be in an addressable storage medium, or may be formed so as to operate one or more processors. Thus, for example, the term "unit" may refer to components such as software components, object-oriented software components, class components, and task components, and may include processes, functions, attributes, procedures, subroutines, segments of program code, drivers, firmware, micro codes, circuits, data, a database, data structures, tables, arrays, or variables. A function provided by the components and "units" may be associated with the smaller number of components and "units", or may be divided into additional components and "units".

In the present specification, an "object" may be a human, an animal, or a part of a human or animal. For example, the object may be an organ (e.g., the liver, the heart, the womb, the brain, a breast, or the abdomen), a blood vessel, or a combination thereof. Furthermore, the "object" may be a phantom. The phantom means a material having a density, an effective atomic number, and a volume that are approximately the same as those of an organism. For example, the phantom may be a spherical phantom having properties similar to the human body.

Furthermore, in the present specification, a "user" may be, but is not limited to, a medical expert, such as a medical doctor, a nurse, a medical laboratory technologist, and a technician who repairs a medical apparatus.

Furthermore, in the present specification, the terms "first", "second", "1-1", etc. are only used to distinguish one component, element, object, image, pixel, or patch from another component, element, object, image, pixel, or patch. Thus, these terms are not limited to representing the order or priority among elements or components. Expressions such as "at least one of," when preceding a list of elements, modify the entire list of elements and do not modify the individual elements of the list.

Reference will now be made in detail to embodiments, examples of which are illustrated in the accompanying drawings. In this regard, the present embodiments may have different forms and should not be construed as being limited to the descriptions set forth herein. In the following description, well-known functions or constructions are not described in detail so as not to obscure the embodiments with unnecessary detail.

FIG. 1 is a conceptual diagram illustrating an example in which an ultrasound diagnosis apparatus 100 detects an ultrasound probe being used by a user, from among wired ultrasound probes 111 and 112 and wireless ultrasound probes 121 and 122, and activates the detected ultrasound probe, according to an embodiment.

Referring to FIG. 1, the ultrasound diagnosis apparatus 100 may be connected with at least one wired ultrasound probe and at least one wireless ultrasound probe. According to an embodiment, the ultrasound diagnosis apparatus 100 may be connected via wire with first and second wired ultrasound probes 111 and 112. Furthermore, the ultrasound diagnosis apparatus 100 may be connected with a plurality of wireless ultrasound probes including first and second wireless ultrasound probes 121 and 122 by using a wireless communication method. Although FIG. 1 shows that the number of the wired ultrasound probes 111 and 112 and the number of the wireless ultrasound probes 121 and 122 are both two (2), embodiments are not limited thereto.

Figure 3:
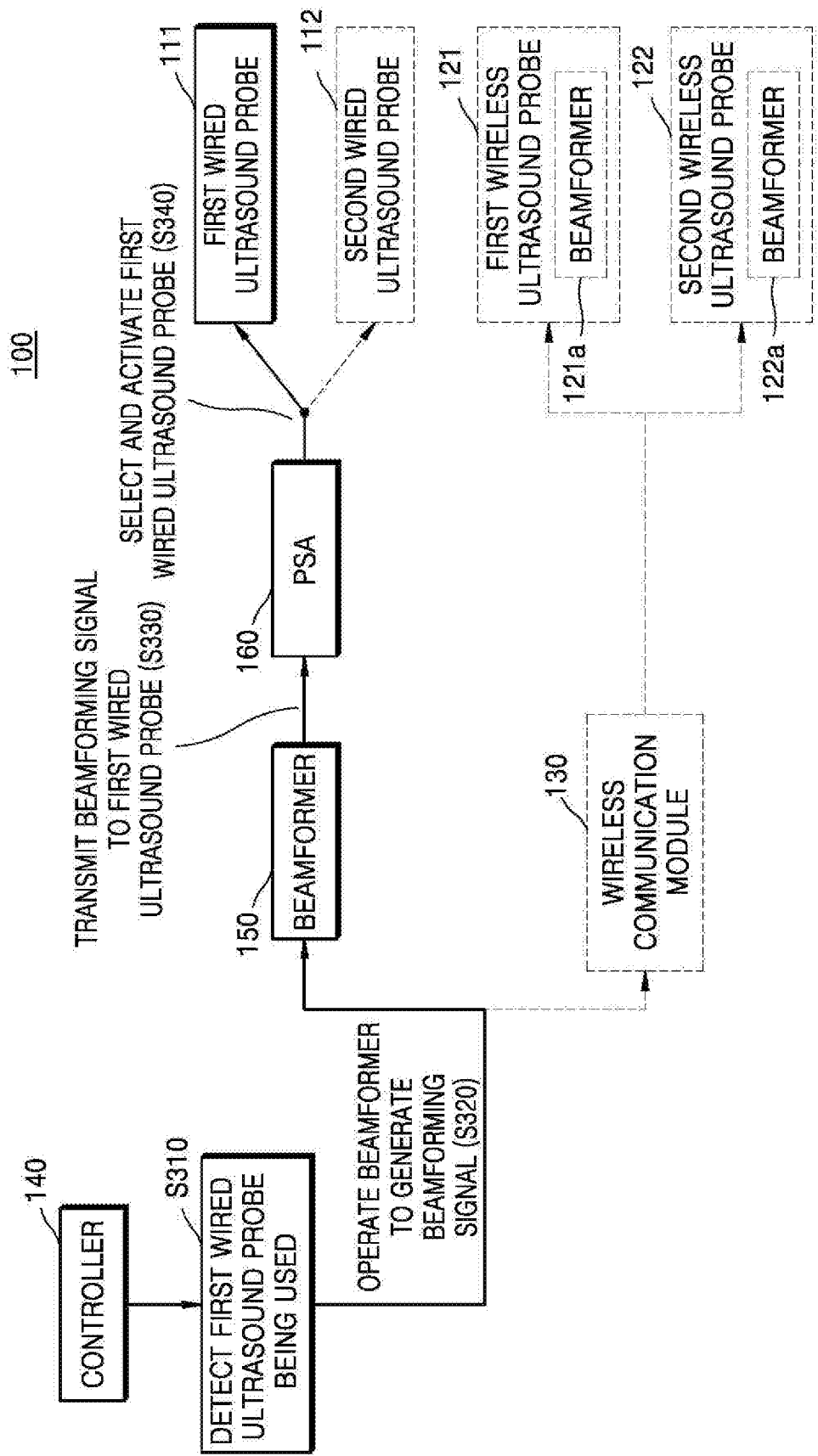
FIG. 3 is a flowchart of a method of operating an ultrasound diagnosis apparatus, according to an embodiment.

In an embodiment, the first and second wired ultrasound probes 111 and 112 may be connected to a controller (140 of FIG. 3) of the ultrasound diagnosis apparatus 100 via a probe switching assembly (PSA, 160 of FIG. 3).

According to an embodiment, the ultrasound diagnosis apparatus 100 may be connected with the first and second wireless ultrasound probes 121 and 122 by using a wireless communication method. In this case, "connected" may mean a state in which the ultrasound diagnosis apparatus 100 is paired to use at least one of the first and second wireless ultrasound probes 121 and 122. Even when the ultrasound diagnosis apparatus 100 is connected with the first and second wireless ultrasound probes 121 and 122, it does not mean that the ultrasound diagnosis apparatus 100 may use all of the first and second wireless ultrasound probes 121 and 122 to transmit ultrasound signals to an object. "Pairing" is conceptually different from "activation", as will be described in more detail below with reference to FIG. 4.

For example, the ultrasound diagnosis apparatus 100 may be connected wirelessly with the first and second wireless ultrasound probes 121 and 122 by receiving pairing reception signals therefrom by using at least one of data communication methods including a Wireless Local Area Network (WLAN), Wireless Fidelity (Wi-Fi), Bluetooth, Zigbee, Wi-Fi Direct (WFD), Infrared Data Association (IrDA), Bluetooth Low Energy (BLE), Near Field Communication (NFC), Wireless Broadband Internet (WiBro), World Interoperability for Microwave Access (WiMAX), Shared Wireless Access Protocol (SWAP), Wireless Gigabit Alliance (WiGig), and radio frequency (RF) communication.

The first and second wireless ultrasound probes 121 and 122 may each transmit ultrasound signals to the object and receive echo signals reflected from the object to thereby produce reception signals. The first and second wireless ultrasound probes 121 and 122 may each perform image processing on the received echo signals to thereby generate ultrasound image data and then transmit the generated ultrasound image data to the controller (140 of FIGS. 2 through 4) of the ultrasound diagnosis apparatus 100.

The ultrasound diagnosis apparatus 100 may detect an ultrasound probe being used by a user 1 to examine the object among the first and second wired ultrasound probes 111 and 112 and the first and second wireless ultrasound probes 121 and 122. According to an embodiment, the ultrasound diagnosis apparatus 100 may detect a user's operation of stopping using the first wired ultrasound probe 111 and then switching probes to use the first wireless ultrasound probe 121 instead. Furthermore, the ultrasound diagnosis apparatus 100 may detect a user's operation of stopping using the first wireless ultrasound probe 121 and then switching probes to use the first wired ultrasound probe 111.

The ultrasound diagnosis apparatus 100 may detect an ultrasound probe being used by the user to examine the object and activate the detected ultrasound probe. In this case, "activation" may mean operating an ultrasound probe to transmit ultrasound signals to the object and receive ultrasound echo signals reflected from the object.

For example, when the ultrasound probe being used by the user 1 is the first wired ultrasound probe 111, the ultrasound diagnosis apparatus 100 may select the first wired ultrasound probe 111 via the PSA (160 of FIG. 3) and transmit a beamforming signal to the selected first wired ultrasound probe 111. The first wired ultrasound probe 111 may then receive the beamforming signal to transmit ultrasound signals to the object and receive ultrasound signals reflected from the object.

As another example, when the ultrasound probe being used by the user 1 is the first wireless ultrasound probe 121, the ultrasound diagnosis apparatus 100 may activate the first wireless ultrasound probe 121 and wirelessly transmit a beamforming control signal for controlling a beamformer included in the first wireless ultrasound probe 121 to the first wireless ultrasound probe 121. The first wireless ultrasound probe 121 may operate the beamformer based on the received beamforming control signal and transmit ultrasound signals generated by the beamformer to the object.

For example, when the user 1 switches the first wireless ultrasound probe 121 being used to use the first wired ultrasound probe 111 instead, the ultrasound diagnosis apparatus 100 may deactivate the first wireless ultrasound probe 121, select the first wired ultrasound probe 111 via the PSA (160 of FIG. 3), and transmit a beamforming signal to the first wired ultrasound probe 111, as will be described in more detail below with reference to FIG. 3.

As another example, when the user 1 switches the first wired ultrasound probe 111 being used to use the first wireless ultrasound probe 121, the ultrasound diagnosis apparatus 100 may deactivate the first wired ultrasound probe 111and wirelessly transmit a beamforming control signal to the beamformer included in the first wireless ultrasound probe 121, as will be described in more detail below with reference to FIG. 4.

Conventionally, ultrasound systems including only wired ultrasound probes or only one wireless ultrasound probe have been used. However, in some cases, a wired ultrasound probe and a wireless ultrasound probe need to be alternately selected for use according to characteristics of an object or a protocol necessary for diagnosing diseases of the object. A conventional ultrasound system including only a wired or wireless ultrasound probe cannot satisfy these needs. Furthermore, even in case of an ultrasound system including both wired and wireless ultrasound probes, when the user quits using the wired ultrasound probe and attempts to use the wireless ultrasound probe, the user suffers the inconvenience of having to manually pair the wireless ultrasound probe and activate the paired wireless ultrasound probe.

The ultrasound diagnosis apparatus 100 includes both at least one wired ultrasound probe (the first and second wired ultrasound probes 111 and 112) and at least one wireless ultrasound probe (the first and second wireless ultrasound probes 121 and 122) and is configured to detect an ultrasound probe being used by the user 1 to examine the object among the first and second wired ultrasound probes 111 and 112 and the first and second wireless ultrasound probes 121 and 122 and activate the detected ultrasound probe directly without a separate pairing process, thereby increasing user convenience. In particular, even when an ultrasound probe being used is switched from a wired ultrasound probe to a wireless ultrasound probe or vice versa, the ultrasound diagnosis apparatus 100 may automatically detect an ultrasound probe being used as a result of switching probes and activate the detected ultrasound probe to transmit ultrasound signals to the object and acquire ultrasound image data from the object.

Figure 2:
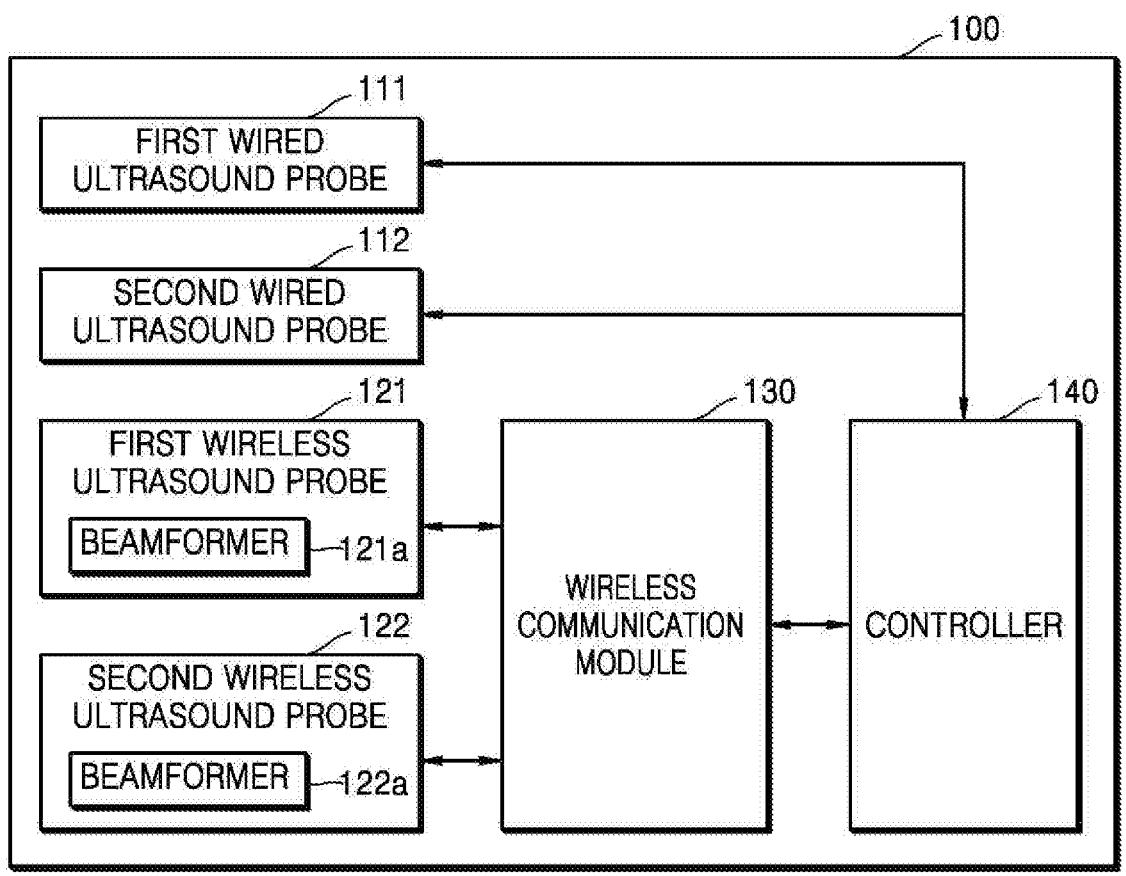
FIG. 2 is a block diagram of a configuration of an ultrasound diagnosis apparatus according to an embodiment.

FIG. 2 is a block diagram of a configuration of an ultrasound diagnosis apparatus 100 according to an embodiment.

Referring to FIG. 2, the ultrasound diagnosis apparatus 100 according to the embodiment may include first and second wired ultrasound probes 111 and 112, first and second wireless ultrasound probes 121 and 122, a wireless communication module 130, and a controller 140. Although FIG. 2 shows that the ultrasound diagnosis apparatus 100 includes the two wired ultrasound probes (the first and second wired ultrasound probes 111 and 112), this is merely an example. The ultrasound diagnosis apparatus 100 may include at least one wired ultrasound probe. Furthermore, although FIG. 2 shows that the ultrasound diagnosis apparatus 100 includes the two wireless ultrasound probes (the first and second wired ultrasound probes 121 and 122), this is merely an example. The ultrasound diagnosis apparatus 100 may include at least one wireless ultrasound probe.

Figure 4:
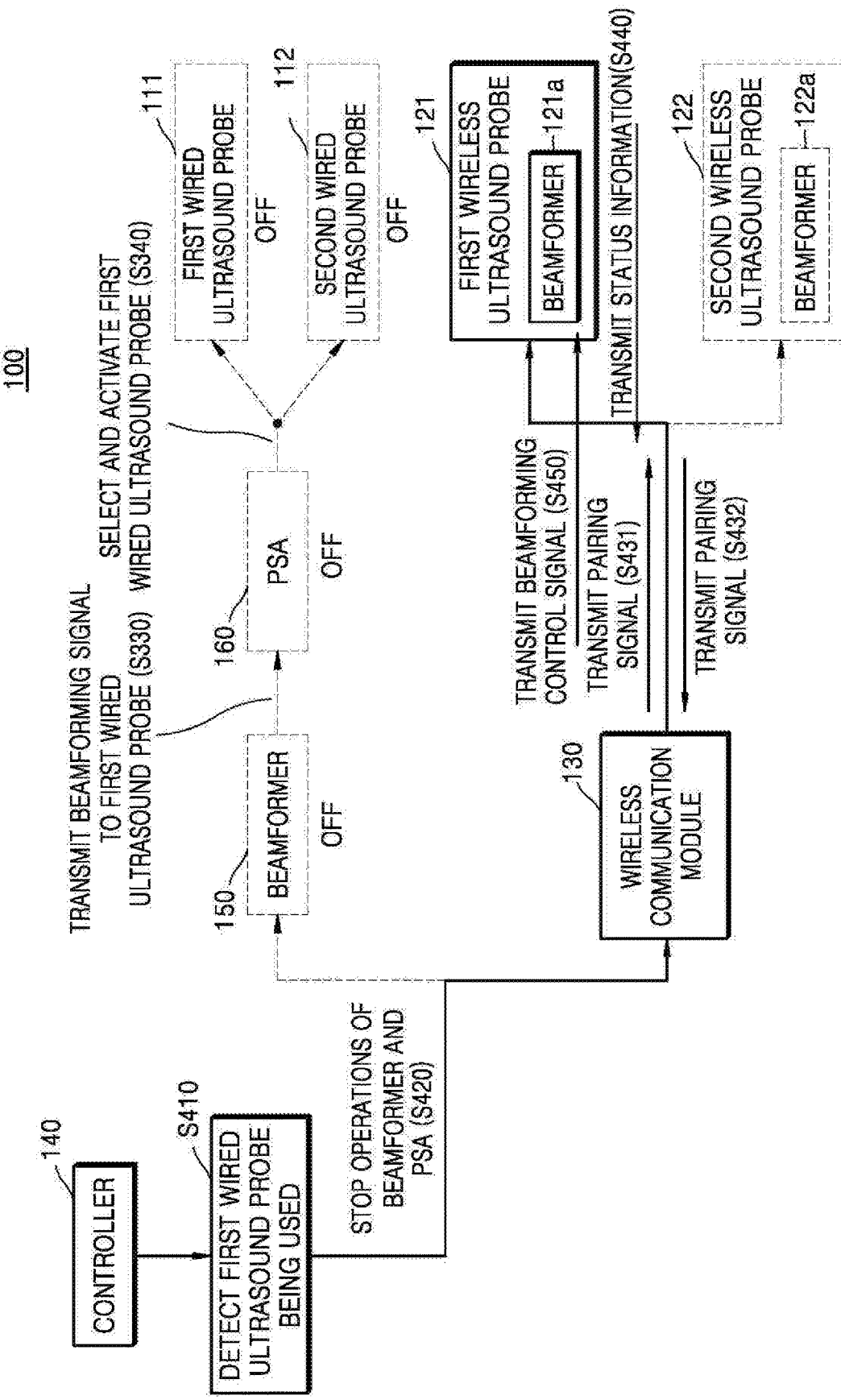
FIG. 4 is a flowchart of a method of operating an ultrasound diagnosis apparatus, according to another embodiment.

According to an embodiment, the ultrasound diagnosis apparatus 100 may further include a beamformer (150 of FIG. 4) and the PCA (160 of FIG. 4).

The ultrasound diagnosis apparatus 100 may be implemented not only as a cart type apparatus but also as a portable type apparatus. Examples of portable ultrasound diagnosis apparatuses may include, but are not limited to, a picture archiving and communication system (PACS) viewer, a hand-carried cardiac ultrasound (HCU) device, a smartphone, a laptop computer, a personal digital assistant (PDA), and a tablet PC.

The first and second wired ultrasound probes 111 and 112 may each include a plurality of transducers for transmitting a beamforming signal generated by the ultrasound diagnosis apparatus 100 to an object. The plurality of transducers included in each of the first and second wired ultrasound probes 111 and 112 may receive ultrasound echo signals reflected from the object to produce reception signals. The first and second wired ultrasound probes 111 and 112 may each transmit the reflected ultrasound echo signals to the controller 140. The controller 140 may then perform analog-to-digital conversion on the received ultrasound echo signals to generate ultrasound image data and perform image processing on the ultrasound image data to obtain an ultrasound image of the object.

The first and second wireless ultrasound probes 121 and 122 may each be different types of probes having different functions, but embodiments are not limited thereto. The first and second wireless ultrasound probes 121 and 122 may each transmit ultrasound signals to the object and receive ultrasound echo signals reflected from the object to produce reception signals.

The first and second wireless ultrasound probes 121 and 122 may respectively include beamformers 121a and 122a for generating ultrasound signals that are transmitted to the object. The beamformers 121a and 122a may each receive a beamforming control signal generated by the controller 140 via the wireless communication module 130 and generate ultrasound signals that are transmitted to the object based on the received beamforming control signal.

The first and second wireless ultrasound probes 121 and 122 may each perform analog-to-digital conversion on received ultrasound echo signals and image processing of the resulting signals to thereby generate ultrasound image data regarding an object. The first and second wireless ultrasound probes 121 and 122 may each transmit generated ultrasound image data to the controller 140 via the wireless communication module 130.

The wireless communication module 130 may receive pairing reception signals from the first and second wireless ultrasound probes 121 and 122 and may be connected simultaneously with the first and second wireless ultrasound probes 121 and 122 by using a wireless communication method based on the pairing reception signals. For example, the wireless communication module 130 may simultaneously be paired wirelessly with the wireless ultrasound probes 201 through 204 by using at least one of wireless communication techniques including a WLAN, Wi-Fi, Bluetooth, Zigbee, WFD, IrDA, BLE, NFC, WiBro, WiMAX, SWAP, WiGig, and RF communication method.

According to an embodiment, the wireless communication module 130 may wirelessly receive pieces of status information regarding the first and second wireless ultrasound probes 121 and 122 based on a control signal from the controller 140. For example, status information may include at least one of a wireless communication frequency, a wireless communication connection type, an executable application, a wireless communication method, a communication status, battery charging information, a remaining battery capacity, and a remaining usability time with respect to each of the first and second wireless ultrasound probes 121 and 122.

According to an embodiment, the wireless communication module 130 may perform data communications with the first and second wireless ultrasound probes 121 and 122 by using a 60-GHz millimeter wave (mmWave) local area communication method. The wireless communication module 130 may receive raw data by using a 60-GHz mmWave wireless communication method. To acquire the raw data, the first and second wireless ultrasound probes 121 and 122 each transmit ultrasound signals to the object, process received ultrasound echo signals, and perform analog-to-digital conversion on the resulting signals.

In another embodiment, the first and second wireless ultrasound probes 121 and 122 may each perform analog-to-digital conversion on received ultrasound echo signals and perform image processing on the analog-to-digital converted signals to generate ultrasound image data. In this case, the wireless communication module 130 may receive the ultrasound image data respectively from the first and second wireless ultrasound probes 121 and 122 via Wi-Fi, WLAN, or Bluetooth.

The controller 140 may control operations of the first wired ultrasound probe 111, the second wired ultrasound probe 112, and the wireless communication module 130. In detail, the controller 140 may activate a wired ultrasound probe being selected and used by a user from among the first and second wired ultrasound probes 111 and 112. In this case, "activation" may mean operating an ultrasound probe to transmit ultrasound signals to the object and receive ultrasound echo signals reflected from the object.

Furthermore, the controller 140 may control the wireless communication module 130 to maintain wireless pairing with the first and second wireless ultrasound probes 121 and 122. Furthermore, the controller 140 may control the wireless communication module 130 to receive pieces of status information from the first and second wireless ultrasound probes 121 and 122. According to an embodiment, the controller 140 may check a status of pairing with each of the first and second wireless ultrasound probes 121 and 122 at preset time intervals. Furthermore, the controller 140 may control the wireless communication module 130 to transmit at preset time intervals a pairing signal for checking whether there is any additional wireless ultrasound probe, other than the first and second wireless ultrasound probes 121 and 122, which is to be wirelessly connected. For example, the controller 140 may control the wireless communication module 130 to transmit a pairing signal for searching for connection of an additional wireless ultrasound probe to a region near the ultrasound diagnosis apparatus 100 at 1-minute or 30-second intervals.

For example, the controller 140 may be formed as a hardware module including at least one of a central processing unit (CPU), a microprocessor, a graphic processing unit, random-access memory (RAM), and read-only memory (ROM). In an embodiment, the controller 140 may be implemented as an application processor (AP). The controller 140 may also be implemented as a hardware component such as a field-programmable gate array (FPGA) or an application-specific integrated circuit (ASIC). However, embodiments are not limited thereto, and the controller 140 may include components such as software components, object-oriented software components, class components and task components, processes, functions, attributes, procedures, subroutines, segments of program code, drivers, firmware, micro codes, circuits, data, a database, data structures, tables, arrays, and variables.

According to an embodiment, the ultrasound diagnosis apparatus 100 may further include a display configured to display a user interface (UI) indicating pieces of status information regarding the first and second wireless ultrasound probes 121 and 122 wirelessly paired thereto.

An operation of the controller 140 activating an ultrasound probe being used by a user, from among the first and second wired ultrasound probes 111 and 112 and the first and second wireless ultrasound probes 121 and 122, according to an embodiment and an operation of the controller 140 activating, when the ultrasound probe being used is switched from a wired ultrasound probe to a wireless ultrasound probe or vice versa, an ultrasound probe being used as a result of the switching according to an embodiment will now be described in detail with reference to FIGS. 3 and 4.

FIGS. 3 and 4 are flowcharts of methods of operating an ultrasound diagnosis apparatus 100, according to embodiments.

Referring to FIGS. 3 and 4, the ultrasound diagnosis apparatus 100 may include first and second wired ultrasound probes 111 and 112, first and second wireless ultrasound probes 121 and 122, a wireless communication module 130, a controller 140, a beamformer 150, and a PSA 160. Since the first and second wired ultrasound probes 111 and 112 and the first and second wireless ultrasound probes 121 and 122, and the wireless communication module 130 correspond to their counterparts of the ultrasound diagnosis apparatus 100 described with reference to FIG. 2, descriptions that are already provided above with respect to FIG. 2 will be omitted herein.

The beamformer 150 may generate a beamforming signal to be applied to a plurality of transducers, which are included in each of the first and second wired ultrasound probes 111 and 112, based on a position and a focal point of the plurality of transducers. The beamformer 150 may transmit a beamforming signal to a wired ultrasound probe selected in response to a control signal from the controller 140.

The PSA 160 may select a wired ultrasound probe detected as being used by a user, from among the first and second wired ultrasound probes 111 and 112. The wired ultrasound probe connected by the PSA 160 among the first and second wired ultrasound probes 111 and 112 may receive a beamforming signal from the beamformer 150 and transmit ultrasound signals to an object based on the received beamforming signal.

An operation of the controller 140 detecting the first wired ultrasound probe 111 being used by the user according to an embodiment is now described.

The controller 140 detects the first wired ultrasound probe 111 being used (operation S310). In an embodiment, the controller 140 may detect the first wired ultrasound probe 111 being used based on a user input signal input via a user input device such as a button, mounted on the first wired ultrasound probe 111. According to an embodiment, the controller 140 may detect the first wired ultrasound probe 111 being used by using a probe information recognition method based on an RF identification (RFID), etc.

In another embodiment, the controller 140 may detect an ultrasound probe being used via a sensor built into the ultrasound probe. The sensor may detect a user input of holding one of the first and second wired ultrasound probes 111 and 112 and the first and second wireless ultrasound probes 121 and 122 in his or her hand. The sensor may then transmit ID information of the detected first wired ultrasound probe 111 to the controller 140, and the controller 140 may identify the first wired ultrasound probe 111 being used based on the received ID information.

The controller 140 generates a beamforming signal by operating the beamformer 150 (operation S320). Since the first and second wireless ultrasound probes 121 and 122 respectively includes beamformers 121a and 122a, when one of the first and second wireless ultrasound probes 121 and 122 is being used, the beamformer 150 may not operate and may be deactivated. The controller 140 may change the deactivated beamformer 150 to an activated state and control the beamformer 150 to generate a beamforming signal.

The controller 140 controls the beamformer 150 to transmit the generated beamforming signal to the first wired ultrasound probe 111 (operation S330). The controller 140 may control the beamformer 150 to transmit the beamforming signal to the first wired ultrasound probe 111 detected as being used, such that the first wired ultrasound probe 111 may emit ultrasound signals toward the object.

The controller 140 controls the PSA 160 to select and activate the first wired ultrasound probe 111 (operation S340). The PSA selects the first wired ultrasound probe 111 among the first and second wired ultrasound probes 111 and 112 based on a control signal from the controller 140 to connect a signal transmission line. The first wired ultrasound probe 111 connected by the PSA 160 may be activated to transmit ultrasound signals to the object and receive ultrasound echo signals reflected from the object.

While performing operations S310, S320, S330, and S340, the controller 140 may control the wireless communication module 130 to maintain wireless pairing respectively with the first and second wireless ultrasound probes 121 and 122. However, the controller 140 does not activate one of the first and second wireless ultrasound probes 121 and 122 to transmit ultrasound signals to the object.

Operations S310, S320, S330, and S340 are part of a method of activating the first wired ultrasound probe 111, and may be applied when an ultrasound probe being used is switched from one of the first and second wireless ultrasound probes 121 and 122 to the first wired ultrasound probe 111 in the same manner as when the first wired ultrasound probe 111 is initially selected and used.

FIG. 4 is a flowchart of a method of operating the ultrasound diagnosis apparatus 100, according to another embodiment.

An operation of the controller 140 detecting the first wireless ultrasound probe 121 being used by the user according to an embodiment will now be described in detail with reference to FIG. 4.

The controller 140 detects the first wireless ultrasound probe 121 being used (operation S410). In an embodiment, the controller 140 may detect the first wireless ultrasound probe 121 being used based on a user input signal input via a user input device such as a button, mounted on the first wireless ultrasound probe 121. According to an embodiment, the controller 140 may detect the first wireless ultrasound probe 121 being used by using a probe information recognition method based on an RFID, etc.

In another embodiment, the controller 140 may detect an ultrasound probe being used via a sensor built into the ultrasound probe. The sensor may detect a user input of holding the first wireless ultrasound probe 121 of the first and second wired ultrasound probes 121 and 122 in his or her hand. The sensor may then transmit ID information of the detected first wireless ultrasound probe 121 to the controller 140, and the controller 140 may identify the first wireless ultrasound probe 121 being used based on the received ID information.

The controller 140 stops operations of the beamformer 150 and the PSA 160 (operation S420). In an embodiment, the controller 140 may switch the beamformer 150 and the PSA 160 to an OFF state by deactivating them. When the beamformer 150 and the PSA 160 are deactivated, operations of the first and second wired ultrasound probes 111 and 112 may also be deactivated. After operation S420, no signal may be transmitted to the first and second wired ultrasound probes 111 and 112.

The controller 140 controls the wireless communication module 130 to transmit a pairing signal to the first wireless ultrasound probe 121 detected as an ultrasound probe being used (operation S431). The wireless communication module 130 may transmit a pairing signal to the first wireless ultrasound probe 121 by using a wireless communication method based on a control signal from the controller 140.

The first wireless ultrasound probe 121 may transmit a pairing signal to the wireless communication module 130 (operation S432).

In operations S431 and S432, the wireless communication module 130 may exchange a pairing signal with the first wireless ultrasound probe 121 by using at least one of wireless communication methods including a WLAN, Wi-Fi, Bluetooth, Zigbee, WFD, IrDA, BLE, NFC, WiBro, WiMAX, SWAP, WiGig, and RF communication.

The first wireless ultrasound probe 121 transmits status information to the wireless communication module 130 (operation S440). According to an embodiment, the controller 140 may control the wireless communication module 130 to receive from the first wireless ultrasound probe 121 status information including at least one of ID information, a wireless communication frequency, a connection type, an executable application, a wireless communication method, battery charging information, a remaining battery capacity, a remaining usability time, and a communication status with respect to the first wireless ultrasound probe 121. Although not shown in FIG. 4, the controller 140 may control the wireless communication module 130 to receive status information from the second wireless ultrasound probe 122 as well.

The controller 140 controls the wireless communication module 130 to transmit a beamforming control signal to the first wireless ultrasound probe 121 (operation S450). A beamforming control signal may be a signal used to control the beamformers 121a and 122b respectively included in the first and second wireless ultrasound probes 121 and 122 to perform beamforming. The controller 140 may generate beamforming control signals for controlling the beamformers 121a and 122a and control the wireless communication module 130 to transmit a beamforming control signal to the beamformer 121a included in the first wireless ultrasound probe 121 detected as being used.

Operations S410, S420, S431, S432, S440, and S450 are part of a method of activating the first wireless ultrasound probe 121, and may be applied when an ultrasound probe being used is switched from one of the first and second wired ultrasound probes 111 and 112 to the first wireless ultrasound probe 121 in the same manner as when the first wireless ultrasound probe 121 is initially selected and used.

According to the embodiments described with reference to FIGS. 3 and 4, the ultrasound diagnosis apparatus 100 is configured to detect an ultrasound probe being used by the user to examine the object among the first and second wired ultrasound probes 111 and 112 and the first and second wireless ultrasound probes 121 and 122 and automatically activate the detected ultrasound probe, thereby eliminating the need to perform unnecessary processes such as a separate wireless pairing process and termination of pairing and thus increasing user convenience.

Figure 5:
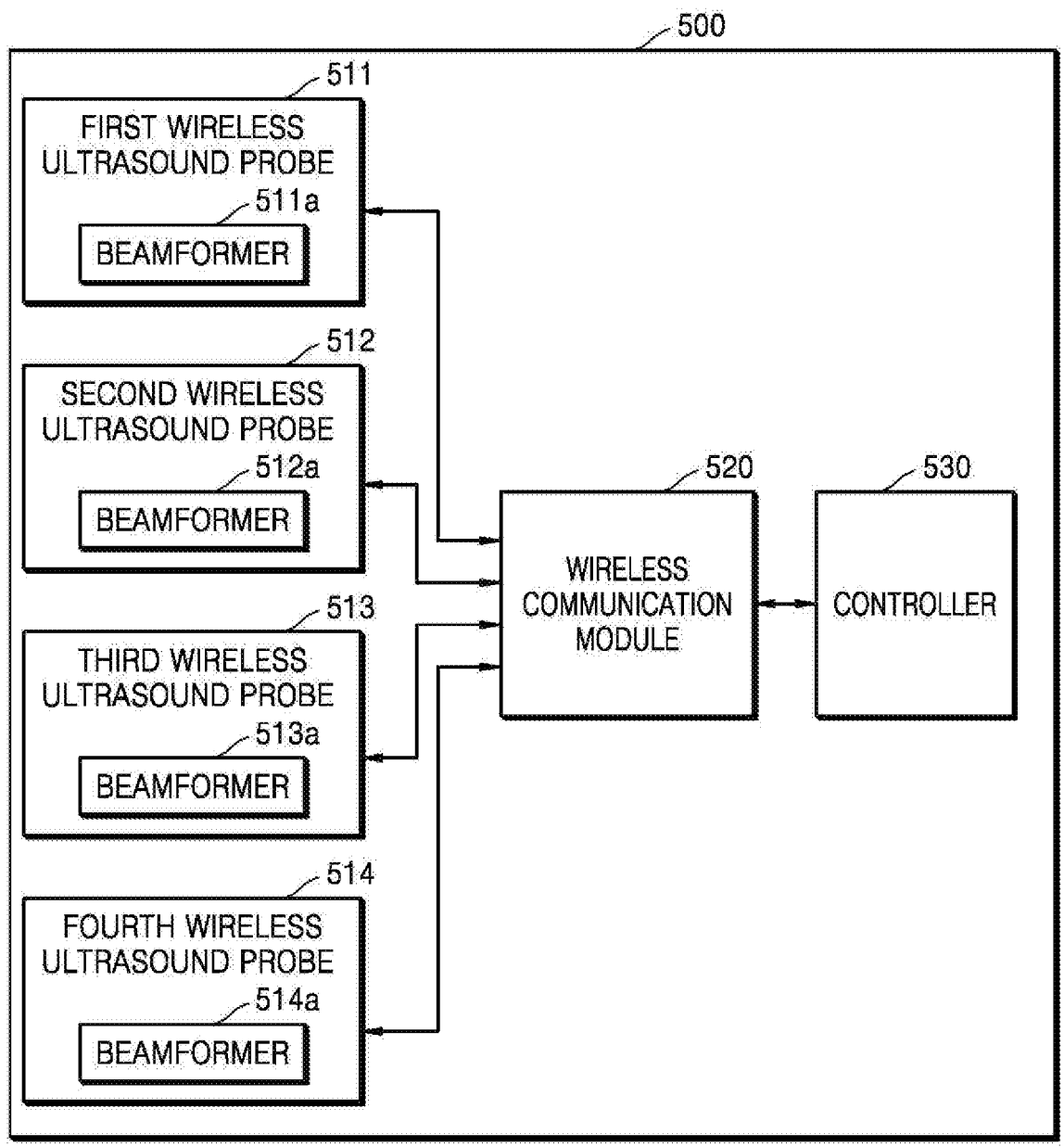
FIG. 5 is a block diagram of a configuration of an ultrasound diagnosis apparatus according to another embodiment.

FIG. 5 is a block diagram of a configuration of an ultrasound diagnosis apparatus 500 according to another embodiment.

Referring to FIG. 5, the ultrasound diagnosis apparatus 500 may include first through fourth wireless ultrasound probes 511 through 514, a wireless communication module 520, and an a controller 530. The ultrasound diagnosis apparatus 500 of FIG. 5 does not include a wired ultrasound probe unlike the ultrasound diagnosis apparatus 200 described with reference to FIG. 2, but includes the same components as their counterparts of the ultrasound diagnosis apparatus 200. Thus, descriptions that are already provided above with respect to FIG. 2 will be omitted herein.

Although a total of four (4) wireless ultrasound probes including the first through fourth wireless ultrasound probes 511 through 514 are shown in FIG. 5, this is merely an example, and the ultrasound diagnosis apparatus 500 may include a plurality of wireless ultrasound probes.

The first through fourth wireless ultrasound probes 511 through 514 may respectively include beamformers 511a through 514a. The beamformers 511a through 514a may each generate a beamforming signal to be applied to a plurality of transducers, which are included in each of the first through fourth wireless ultrasound probes 511 through 514, based on a position and a focal point of the plurality of transducers.

The first through fourth wireless ultrasound probes 511 through 514 may each perform analog-to-digital conversion on received ultrasound echo signals and perform image processing on the analog-to-digital converted signals to thereby generate ultrasound image data. The first through fourth wireless ultrasound probes 511 through 5'4 may each transmit the generated ultrasound image data to the controller 530 via the wireless communication module 520.

The first through fourth wireless ultrasound probes 511 through 514 may each be connected with the wireless communication module 520 by using a wireless communication method. For example, the first through fourth wireless ultrasound probes 511 through 514 may be wirelessly paired with the wireless communication module 520 by using at least one of wireless communication techniques including a WLAN, Wi-Fi, Bluetooth, Zigbee, WFD, IrDA, BLE, NFC, WiBro, WiMAX, SWAP, WiGig, and RF communication method.

The wireless communication module 520 may be connected with the first through fourth wireless ultrasound probes 511 through 514 by using a wireless communication method. The wireless communication module 520 may be simultaneously paired wirelessly with the first through fourth wireless ultrasound probes 511 through 514.

According to an embodiment, the wireless communication module 520 may wirelessly receive status information regarding each of the first through fourth wireless ultrasound probes 511 through 514 based on a control signal from the controller 530. For example, the wireless communication module 520 may receive from the first wireless ultrasound probe 511 status information including at least one of ID information, a wireless communication frequency, a connection type, an executable application, a wireless communication method, battery charging information, a remaining battery capacity, a remaining usability time, and a communication status with respect to the first wireless ultrasound probe 511.

According to an embodiment, the wireless communication module 520 may perform data communication with each of the first through fourth wireless ultrasound probes 511 through 514 by using a 60-GHz mmWave local area wireless communication method. The wireless communication module 520 may receive raw data by using a 60-GHz mmWave wireless communication method. To acquire the raw data, each of the first through fourth wireless ultrasound probes 511 through 514 transmits ultrasound signals to the object, processes received ultrasound echo signals, and performs analog-to-digital conversion on the resulting signals.

The controller 530 may detect a wireless ultrasound probe being used by the user among the first through fourth wireless ultrasound probes 511 through 514 wirelessly paired with the wireless communication module 520 and control the wireless communication module 520 to transmit an activation signal to the detected wireless ultrasound probe. According to an embodiment, the controller 530 may detect the first wireless ultrasound probe 511 being used based on a user input signal input via a user input device such as a button, mounted on the first wireless ultrasound probe 511. According to an embodiment, the controller 530 may detect the first wireless ultrasound probe 511 being used by using a probe information recognition method based on an RFID, etc.

In another embodiment, the controller 530 may detect an ultrasound probe being used via a sensor built into the ultrasound probe. The sensor may detect a user input of holding in his or her hand the first wireless ultrasound probe 511 among the first through fourth wireless ultrasound probes 511 through 514. The sensor may then transmit ID information of the detected first wireless ultrasound probe 511 to the controller 530, and the controller 530 may detect the first wireless ultrasound probe 511 being used based on the received ID information.

The controller 530 may control the wireless communication module 520 to transmit a beamforming control signal for controlling the beamformer 511a included in the detected first wireless ultrasound probe 511 to the first wireless ultrasound probe 511. The first wireless ultrasound probe 511 that has received the beamforming control signal from the controller 530 may generate ultrasound transmitting signals via the beamformer 511a and transmit the generated ultrasound transmitting signals to the object via a plurality of transducers included therein.

The controller 530 may be constructed by a hardware module including at least one of a CPU, a microprocessor, a graphic processing unit, RAM, ROM, and an AP.

Although not shown in FIG. 5, the ultrasound diagnosis apparatus 100 may further include a display configured to display a UI indicating ID information and status information regarding each of the first through fourth wireless ultrasound probes 511 through 514.

The ultrasound diagnosis apparatus 500 according to the embodiment may include a plurality of wireless ultrasound probes, i.e., the first through fourth wireless ultrasound probes 511 through 514 and may simultaneously be wirelessly paired therewith. Furthermore, the ultrasound diagnosis apparatus 500 is configured to detect a wireless ultrasound probe being used among the paired first through fourth wireless ultrasound probes 511 through 514 and automatically transmit an activation signal to the detected wireless ultrasound probe, thereby eliminating the need to perform an unnecessary pairing process and therefore increasing user convenience.

Figure 6:
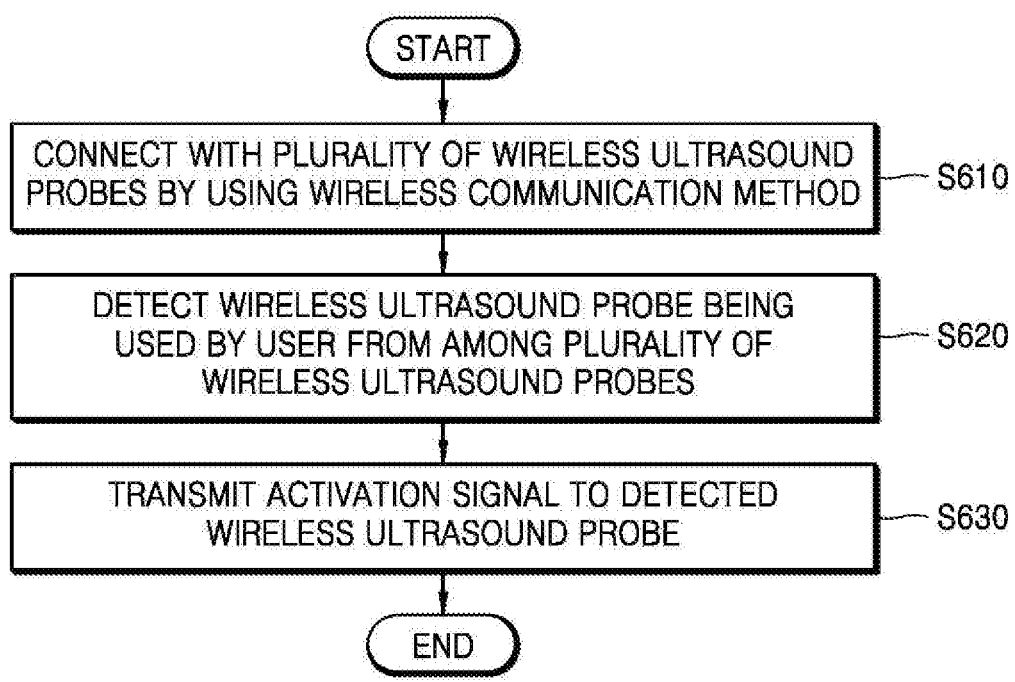
FIG. 6 is a flowchart of a method of operating an ultrasound diagnosis apparatus, according to another embodiment.

FIG. 6 is a flowchart of a method of operating an ultrasound diagnosis apparatus, according to another embodiment.

The ultrasound diagnosis apparatus is connected with a plurality of different wireless ultrasound probes by using a wireless communication method (operation S610). According to an embodiment, the plurality of wireless ultrasound probes may each be different types of wireless ultrasound probes having different functions, but are not limited thereto. The wireless ultrasound probes may be the same type of wireless ultrasound probes. In an embodiment, the ultrasound diagnosis apparatus may be connected wirelessly with the wireless ultrasound probes by using at least one of wireless communication methods including WLAN, Wi-Fi, Bluetooth, Zigbee, WFD, IrDA, BLE, NFC, WiBro, WiMAX, SWAP, WiGig, and RF communication. In operation S610, "connected" may mean a state in which the ultrasound diagnosis apparatus is paired to use at least one of the wireless ultrasound probes. In an embodiment, the ultrasound diagnosis apparatus may be paired simultaneously with the wireless ultrasound probes.

The ultrasound diagnosis apparatus detects a wireless ultrasound probe being used by a user, from among the wireless ultrasound probes (operation S620). The ultrasound diagnosis apparatus may detect a wireless ultrasound probe being used based on a user input signal input via a user input device such as a button, mounted on each of the wireless ultrasound probes. According to an embodiment, the ultrasound diagnosis apparatus may detect the wireless ultrasound probe being used by using a probe information recognition method based on an RFID, etc.

The ultrasound diagnosis apparatus transmits an activation signal to the detected wireless ultrasound probe (operation S630). In this case, "activation" is conceptually different from the "connection" or "pairing" in operation S610 and means operating the detected wireless ultrasound probe to transmit ultrasound signals to an object and receive ultrasound echo signals reflected from the object to thereby generate ultrasound image data.

According to an embodiment, each of the wireless ultrasound probes may include a beamformer. The ultrasound diagnosis apparatus may generate a beamforming control signal for controlling a beamformer included in the wireless ultrasound probe detected in operation S620 and transmit the generated beamforming control signal to the detected wireless ultrasound probe. The wireless ultrasound probe that has received the beamforming control signal may generate ultrasound transmitting signals via the beamformer and transmit the generated ultrasound transmitting signals to the object via a plurality of transducers included therein.

According to an embodiment, the activated wireless ultrasound probe may perform analog-to-digital conversion and image processing on ultrasound echo signals reflected from the object to generate ultrasound image data and transmit the generated ultrasound image data to the ultrasound diagnosis apparatus. In this case, the wireless ultrasound probe may transmit the ultrasound image data, i.e., ultrasound raw data to the ultrasound diagnosis apparatus by using a 60-GHz mmWave local area wireless communication method.

Figure 7:
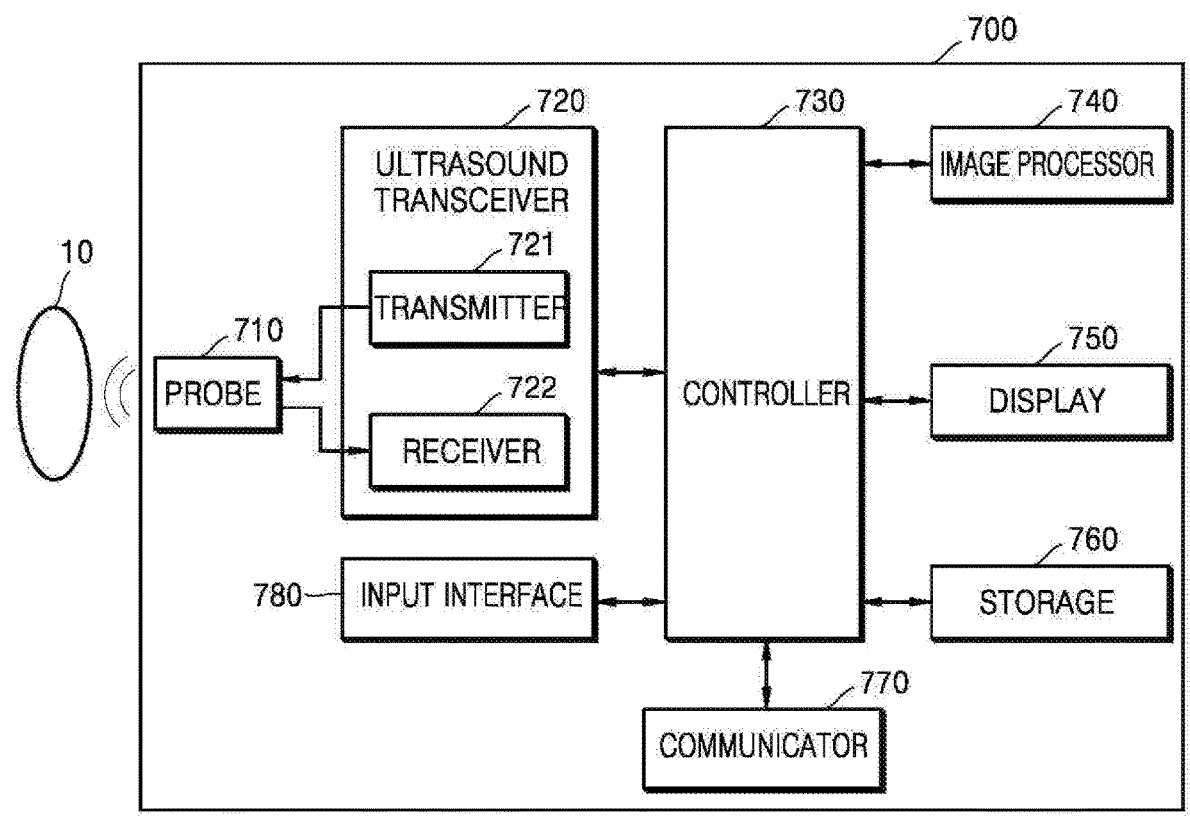
FIG. 7 is a block diagram of a configuration of an ultrasound diagnosis apparatus including a wired ultrasound probe, according to an embodiment.

FIG. 7 is a block diagram of a configuration of an ultrasound diagnosis apparatus 700 including a wired ultrasound probe 710, according to an embodiment;

Referring to FIG. 7, the ultrasound diagnosis apparatus 700 may include the wired ultrasound probe 710, an ultrasound transceiver 720, a controller 730, an image processor 740, a display 750, a storage 760, a communicator 770, and an input interface 780.

The ultrasound diagnosis apparatus 700 may be implemented not only as a cart type apparatus but also as a portable type apparatus. Examples of a portable ultrasound diagnosis apparatus may include, but are not limited to, a smartphone, a laptop computer, a PDA, and a tablet PC.

The wired ultrasound probe 710 may include a plurality of transducers. The plurality of transducers may transmit ultrasound signals to an object 10 in response to transmitting signals received from a transmitter 721. The plurality of transducers may receive ultrasound signals reflected from the object 10 to generate reception signals. Furthermore, the wired ultrasound probe 710 may be formed integrally with the ultrasound diagnosis apparatus 700, or the wired ultrasound probe 710 and the ultrasound diagnosis apparatus 700 may be formed separately but connected to each other by wire or wirelessly. In addition, the ultrasound diagnosis apparatus 700 may include one or more wired ultrasound probes 710 according to embodiments.

The controller 730 may control the transmitter 721 to generate transmitting signals to be respectively applied to the plurality of transducers based on a position and a focal point of the plurality of transducers included in the wired ultrasound probe 710.

The controller 730 may control the ultrasound receiver 722 to generate ultrasound data by performing analog-to-digital conversion on reception signals received from the wired ultrasound probe 710 and summing the analog-to-digital converted reception signals based on a position and a focal point of the plurality of transducers.

The image processor 740 may generate an ultrasound image by using the ultrasound data generated by the ultrasound receiver 722.

The display 750 may display the generated ultrasound image and various pieces of information processed by the ultrasound diagnosis apparatus 700. The ultrasound diagnosis apparatus 700 may include one or a plurality of displays 750 according to its implemented configuration. The display 750 may be combined with a touch panel to form a touch screen.

The controller 730 may control all the operations of the ultrasound diagnosis apparatus 700 and flow of signals between the internal elements of the ultrasound diagnosis apparatus 700. The controller 730 may include a memory for storing a program or data to perform functions of the ultrasound diagnosis apparatus 700 and a processor for processing the program or data. For example, the controller 730 may control the operation of the ultrasound diagnosis apparatus 700 by receiving a control signal from the input interface 780 or an external apparatus.

The ultrasound diagnosis apparatus 700 may include the communicator 770 and may be connected to external apparatuses, for example, servers, medical apparatuses, and portable devices such as smart phones, tablet PCs, wearable devices, etc., via the communicator 770.

The communicator 770 may include at least one element that enables communication with the external apparatuses. For example, the communicator 770 may include at least one of a local area communication module, a wired communication module, and a wireless communication module.

The communicator 770 may receive a control signal and data from an external apparatus and transmit the received control signal to the controller 730 such that the controller 730 may control the ultrasound diagnosis apparatus 700 in response to the received control signal.

The controller 730 may also transmit a control signal to the external apparatus via the communicator 770 such that the external apparatus may be controlled in response to the control signal from the controller 730.

For example, the external apparatus may process data of the external apparatus in response to the control signal from the controller 730 received via the communicator 770.

A program for controlling the ultrasound diagnosis apparatus 700 may be installed in the external apparatus. The program may include command languages for performing part of operation of the controller 730 or the entire operation thereof.

The program may be pre-installed in the external apparatus or may be installed by a user of the external apparatus by downloading the program from a server that provides applications. The server that provides applications may include a recording medium where the program is stored.

The storage 760 may store various pieces of data or programs for driving and controlling the ultrasound diagnosis apparatus 700, input and/or output ultrasound data, obtained ultrasound images, etc.

The input interface 780 may receive a user input for controlling the ultrasound diagnosis apparatus 700. For example, the user input may include an input for manipulating a button, a keypad, a mouse, a trackball, a jog switch, or a knob, an input for touching a touchpad or a touch screen, a voice input, a motion input, and an input of biometric information such as iris recognition or fingerprint recognition, but embodiments are not limited thereto.

Figure 8:
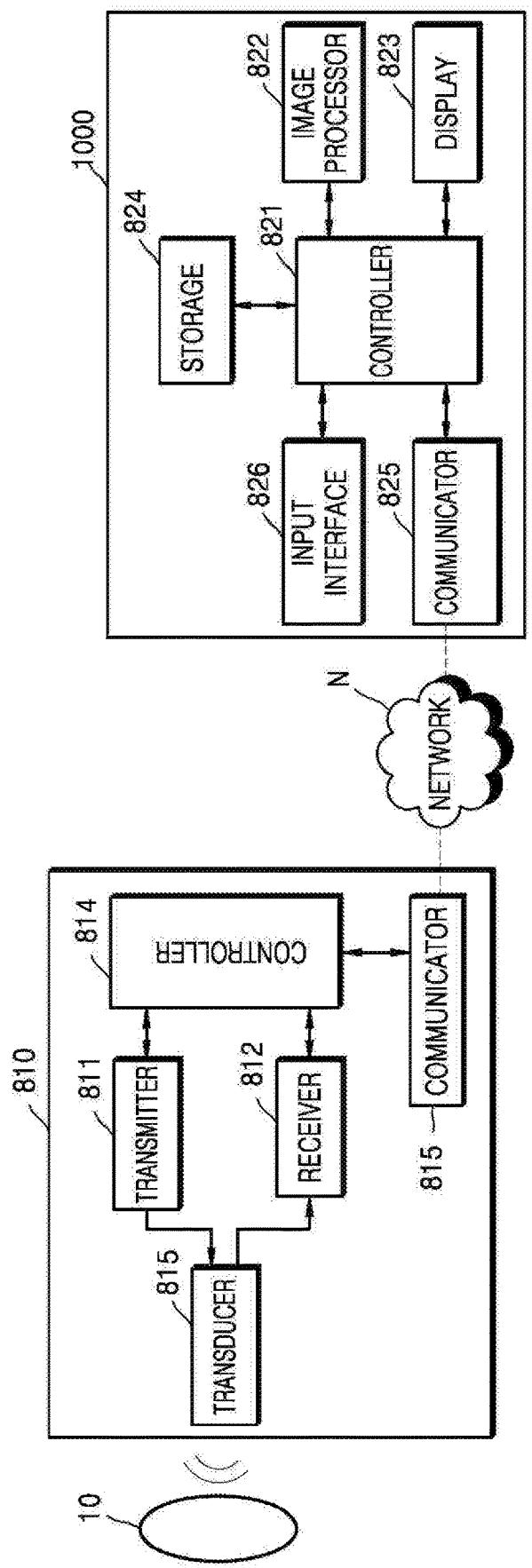
FIG. 8 is a block diagram of a configuration of an ultrasound diagnosis system including a wireless ultrasound probe, according to an embodiment.

FIG. 8 is a block diagram of a configuration of an ultrasound system 800 including a wireless ultrasound probe 810, according to an embodiment.

Referring to FIG. 8, an ultrasound diagnosis apparatus 820 may be connected with the wireless ultrasound probe 800 via a network N.

The wireless ultrasound probe 810 may include a transmitter 811, a receiver 812, a transducer 813, a controller 814, and a communicator 815. Although FIG. 8 shows that the wireless ultrasound probe 810 includes both the transmitter 811 and the receiver 812, according to an implemented configuration, the wireless ultrasound probe 810 may include some of the components of the transmitter 811 and the receiver 812 while the ultrasound diagnosis apparatus 820 may also include some of the components thereof.

The transducer 813 may include a plurality of transducer elements. The plurality of transducer elements may transmit ultrasound signals to an object 10 in response to transmitting signals received from the transmitter 811. The transducer elements may receive ultrasound signals reflected from the object 10 to generate reception signals.

The controller 814 controls the transmitter 811 to generate transmitting signals to be respectively applied to the transducer elements based on positions and focal points of the transducer elements.

The controller 814 controls the receiver 812 to generate ultrasound data by performing analog-to-digital conversion on the reception signals received from the transducer 813 and summing the analog-to-digital converted reception signals based on a position and a focal point of the transducer elements.

The communicator 815 may wirelessly transmit the generated ultrasound data or ultrasound image to the ultrasound diagnosis apparatus 820 via a wireless network. Alternatively, the communicator 815 may receive a control signal and data from the ultrasound diagnosis apparatus 820.

The ultrasound diagnosis apparatus 820 may receive ultrasound data or an ultrasound image from the wireless ultrasound probe 810. The ultrasound diagnosis apparatus 820 may include a controller 821, an image processor 822, a display 823, and a storage 824, a communicator 825, and an input interface 826.

The controller 821 may control all operations of the ultrasound diagnosis apparatus 820 and flow of signals between the internal elements of the ultrasound diagnosis apparatus 820. The controller 821 may include a memory for storing a program or data to perform functions of the ultrasound diagnosis apparatus 820 and a processor for processing the program or data. Furthermore, the controller 821 may control the operation of the ultrasound diagnosis apparatus 820 by receiving a control signal from the input interface 826 or an external apparatus.

The ultrasound diagnosis apparatus 820 may include the communicator 825 and may be connected to external apparatuses, for example, servers, medical apparatuses, and portable devices such as smart phones, tablet PCs, wearable devices, etc., via the communicator 825.

The communicator 825 may include at least one element capable of communicating with the external apparatuses. For example, the communicator 825 may include at least one of a local area communication module, a wired communication module, and a wireless communication module.

The communicator 825 may receive a control signal and data from an external apparatus and transmit the received control signal to the controller 821 such that the controller 821 may control the ultrasound diagnosis apparatus 820 in response to the received control signal.

Alternatively, the controller 821 may transmit a control signal to the external apparatus via the communicator 825 to control the external apparatus in response to the control signal from the controller 821.

For example, the external apparatus may process data from the external apparatus in response to the control signal from the controller 821 received via the communicator 825.

A program for controlling the ultrasound diagnosis apparatus 820 may be installed in the external apparatus. The program may include command languages for performing part of operation of the controller 821 or the entire operation thereof.

The program may be pre-installed in the external apparatus or may be installed by a user of the external apparatus by downloading the program from a server that provides applications. The server that provides applications may include a recording medium on which the program is stored.

The image processor 822 may generate an ultrasound image by using ultrasound data received from the wireless ultrasound probe 810.

The display 823 may display an ultrasound image received from the wireless ultrasound probe 810 and an ultrasound image generated by the ultrasound diagnosis apparatus 820. The ultrasound diagnosis apparatus 820 may include two or more displays 823 according to its implemented configuration. Furthermore, the display 823 may be combined with a touch panel to form a touch screen.

The storage 824 may store various pieces of data or programs for driving and controlling the ultrasound diagnosis apparatus 820, input and/or output ultrasound data, ultrasound images, etc.

The input interface 826 receives a user input for controlling the ultrasound diagnosis apparatus 820. For example, the user input may include an input for manipulating a button, a keypad, a mouse, a trackball, a jog switch, or a knob, an input for touching a touchpad or a touch screen, a voice input, a motion input, and an input of biometric information such as iris recognition or fingerprint recognition, but embodiments are not limited thereto.

Figure 9C:
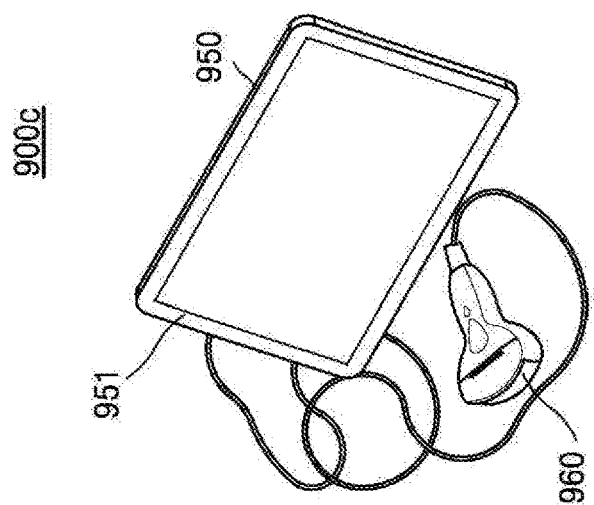
FIGS. 9A through 9C are diagrams illustrating ultrasound diagnosis apparatuses.
Figure 9B:
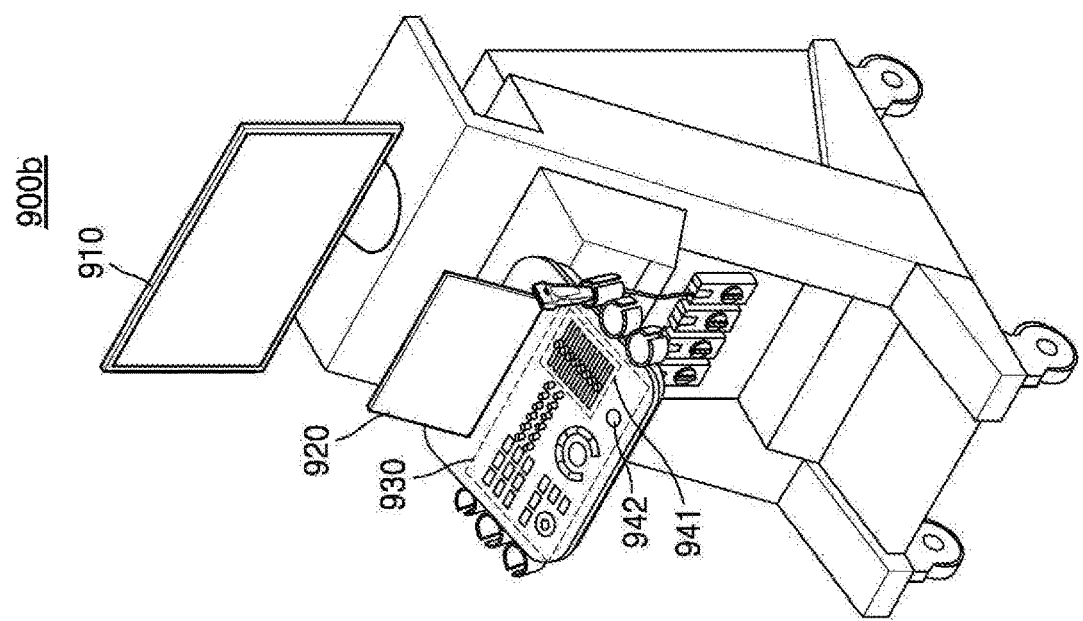
Figure 9A:
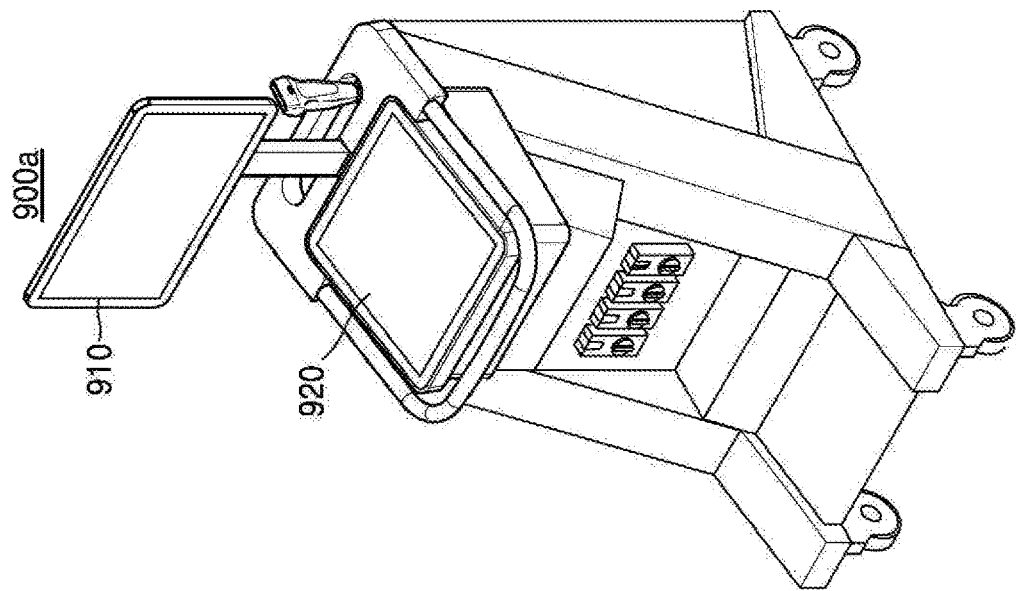

FIGS. 9A, 9B, and 9C are diagrams illustrating ultrasound diagnosis apparatus according to an exemplary embodiment.

Referring to FIGS. 9A and 9B, the ultrasound diagnosis apparatuses 900a and 900b may include a main display 910 and a sub-display 920. At least one among the main display 910 and the sub-display 920 may include a touch screen. The main display 910 and the sub-display 920 may display ultrasound images and/or various information processed by the ultrasound diagnosis apparatuses 900a and 900b. The main display 910 and the sub-display 920 may provide graphical user interfaces (GUI), thereby receiving user's inputs of data to control the ultrasound diagnosis apparatuses 900a and 900b. For example, the main display 910 may display an ultrasound image and the sub-display 920 may display a control panel to control display of the ultrasound image as a GUI. The sub-display 920 may receive an input of data to control the display of an image through the control panel displayed as a GUI. The ultrasound diagnosis apparatuses 900a and 900b may control the display of the ultrasound image on the main display 910 by using the input control data.

Referring to FIG. 9B, the ultrasound diagnosis apparatus 900b may include a control panel 930. The control panel 930 may include buttons, trackballs, jog switches, or knobs, and may receive data to control the ultrasound diagnosis apparatus 900b from the user. For example, the control panel 930 may include a time gain compensation (TGC) button 941 and a freeze button 942. The TGC button 941 is to set a TGC value for each depth of an ultrasound image. Also, when an input of the freeze button 942 is detected during scanning an ultrasound image, the ultrasound diagnosis apparatus 900b may keep displaying a frame image at that time point.

The buttons, trackballs, jog switches, and knobs included in the control panel 930 may be provided as a GUI to the main display 910 or the sub-display 920.

Referring to FIG. 9C, the ultrasound diagnosis apparatus 900c may include a portable device. An example of the portable ultrasound diagnosis apparatus 900c may include, for example, smart phones including probes and applications, laptop computers, personal digital assistants (PDAs), or tablet PCs, but an exemplary embodiment is not limited thereto.

The ultrasound diagnosis apparatus 900c may include the probe 960 and a main body 950. The probe 960 may be connected to one side of the main body 950 by wire or wirelessly. The main body 950 may include a touch screen 951. The touch screen 951 may display an ultrasound image, various pieces of information processed by the ultrasound diagnosis apparatus 900c, and a GUI.

The embodiments of the present disclosure can be written as computer programs and can be implemented in general-use digital computers that execute the programs using a computer-readable recording medium. The above-described embodiments of the present disclosure may be embodied in form of a computer-readable recording medium for storing computer executable command languages and data. The command languages may be stored in form of program codes and, when executed by a processor, may perform a certain operation by generating a certain program module. Also, when executed by a processor, the command languages may perform certain operations of the disclosed embodiments.

Examples of the computer-readable recording medium include magnetic storage media (e.g., ROM, floppy disks, hard disks, etc.), optical recording media (e.g., CD-ROMs or DVDs), etc.

While the present disclosure has been particularly shown and described with reference to exemplary embodiments thereof, it will be understood by those of ordinary skill in the art that various changes in form and details may be made therein without departing from the spirit and scope of the present disclosure as defined by the following claims. Accordingly, the above embodiments and all aspects thereof are examples only and are not limiting.

What is claimed is:

1. An ultrasound diagnosis apparatus comprising:
at least one wired ultrasound probe connected via wire to the ultrasound diagnosis apparatus;
at least one wireless ultrasound probe connected to the ultrasound diagnosis apparatus by using wireless communication;
a wireless communicator configured to receive a pairing reception signal from the at least one wireless ultrasound probe to thereby be connected with the at least one wireless ultrasound probe by using a wireless communication method;
a probe switching assembly configured to select a wired ultrasound probe from among the at least one wired ultrasound probe by connecting a signal transmission line to the wired ultrasound probe; and
a controller configured to:
control the wireless communicator to transmit and receive a beamforming control signal and ultrasound image data to and from each of the at least one wireless ultrasound probe,
detect an ultrasound probe being selected by a user to examine an object, from among the at least one wired ultrasound probe and the at least one wireless ultrasound probe, and
activate the detected ultrasound probe,
wherein the controller is further configured to control the probe switching assembly to select a wired ultrasound probe from among the at least one wired ultrasound probe, and activate the selected wired ultrasound probe, and
wherein the controller is further configured to deactivate an operation of the probe switching assembly when the ultrasound probe detected as being selected by the user is a wireless ultrasound probe from among the at least one wireless ultrasound probe.

2. The ultrasound diagnosis apparatus of claim 1, further comprising:
a beamformer configured to generate a beamforming signal to be applied to each of a plurality of transducers included in each of at least one wired ultrasound probe, based on a position and a focal point of the plurality of transducers.

3. The ultrasound diagnosis apparatus of claim 2, wherein the controller is further configured to control the beamformer to transmit the beamforming signal to the wired ultrasound probe.

4. The ultrasound diagnosis apparatus of claim 2, wherein the controller is further configured to stop operations of the beamformer when the ultrasound probe detected as being selected is switched from the wired ultrasound probe activated among the at least one wired ultrasound probe to one of the at least one wireless ultrasound probe.

5. The ultrasound diagnosis apparatus of claim 4, wherein the controller is further configured to resume, when the ultrasound probe detected as being selected is switched from the wireless ultrasound probe to the wired ultrasound probe, the operations of the beamformer and the probe switching assembly, control the probe switching assembly to activate the wired ultrasound probe, and control the beamformer to transmit the beamforming signal to the wired ultrasound probe.

6. The ultrasound diagnosis apparatus of claim 1, wherein the controller is further configured to control the wireless communicator to transmit, when the ultrasound probe detected as being selected is a wireless ultrasound probe, a beamforming control signal for controlling a beamformer included in the wireless ultrasound probe to the wireless ultrasound probe.

7. The ultrasound diagnosis apparatus of claim 1, wherein the controller is further configured to control the wireless communicator to receive, from the at least one wireless ultrasound probe, status information including at least one of identification information, a wireless communication frequency, a connection type, an executable application, a wireless communication method, battery charging information, a remaining battery capacity, a remaining usability time, and a communication status with respect to each of the at least one wireless ultrasound probe.

8. The ultrasound diagnosis apparatus of claim 1, wherein the controller is further configured to control the wireless communicator to connect with the at least one wireless ultrasound probe by using at least one of wireless communication methods comprising a Wireless Local Area Network (WLAN), wireless fidelity (Wi-Fi), Bluetooth, Zigbee, Wi-Fi Direct (WFD), Infrared Data Association (IrDA), Bluetooth Low Energy (BLE), Near Field Communication (NFC), Wireless Broadband Internet (WiBro), World Interoperability for Microwave Access (WiMAX), Shared Wireless Access Protocol (SWAP), Wireless Gigabit Alliance (WiGig), and radio frequency (RF) communication.

9. The ultrasound diagnosis apparatus of claim 1, wherein the controller is further configured to control the wireless communicator to perform pairing simultaneously with the at least one wireless ultrasound probe.

10. The ultrasound diagnosis apparatus of claim 1, wherein the controller is further configured to check a status of wireless connection between the ultrasound diagnosis apparatus and the at least one wireless ultrasound probe at preset time intervals.

11. An ultrasound diagnosis apparatus comprising:
a wireless communicator; and
a controller configured to:
control the wireless communicator to connect with each of a plurality of different wireless ultrasound probes by using a wireless communication method,
detect a wireless ultrasound probe being selected by a user, from among the plurality of wireless ultrasound probes, and
control the wireless communicator to transmit, to the detected wireless ultrasound probe, an activation signal and a beamforming control signal for controlling a beamformer included in the detected wireless ultrasound probe.

12. The ultrasound diagnosis apparatus of claim 11, wherein the controller is further configured to control the wireless communicator to transmit and receive a pairing signal to and from each of the plurality of wireless ultrasound probes by using a wireless communication method.

13. The ultrasound diagnosis apparatus of claim 11, wherein the controller is further configured to control the wireless communicator to receive, from the plurality of wireless ultrasound probes, status information including at least one of identification information, a wireless communication frequency, a connection type, an executable application, a wireless communication method, battery charging information, a remaining battery capacity, a remaining usability time, and a communication status with respect to each of the plurality of wireless ultrasound probes.

14. The ultrasound diagnosis apparatus of claim 11, wherein the controller is further configured to control the wireless communicator to perform pairing simultaneously with the plurality of wireless ultrasound probes.

15. A method of operating an ultrasound diagnosis apparatus comprising at least one wired ultrasound probe and at least one wireless ultrasound probe, the method comprising:
connecting the ultrasound diagnosis apparatus with the at least one wireless ultrasound probe by using a wireless communication method;
detecting an ultrasound probe being selected by a user to examine an object, from among the at least one wired ultrasound probe and the at least one wireless ultrasound probe; and
activating the detected ultrasound probe,
wherein the activating of the detected ultrasound probe comprises:
detecting a first wired ultrasound probe being selected, from among the at least one wired ultrasound probe; and
controlling a probe switching assembly included in the ultrasound diagnosis apparatus to activate the first wired ultrasound probe,
wherein the activating of the detected ultrasound probe comprises deactivating an operating of the probe switching assembly when the ultrasound probe detected as being selected by the user is a wireless ultrasound probe from among the at least one wireless ultrasound probe.

16. The method of claim 15, wherein the activating of the detected ultrasound probe further comprises transmitting a beamforming signal to the first wired ultrasound probe.

17. The method of claim 16, further comprising stopping transmission of the beamforming signal when the ultrasound probe detected as being selected is switched from the first wired ultrasound probe to one of the at least one wireless ultrasound probe.

18. The method of claim 17, further comprising:
resuming, when the ultrasound probe detected as being selected is switched from the wireless ultrasound probe to a second wired ultrasound probe, the operation of the probe switching assembly to activate the second wired ultrasound probe; and
transmitting the beamforming signal to the second wired ultrasound probe.

19. The method of claim 15, wherein the activating of the detected ultrasound probe comprises:
detecting a first wireless ultrasound probe being selected, from among the at least one wireless ultrasound probe; and
transmitting a beamforming control signal for controlling a beamformer included in the first wireless ultrasound probe to the first wireless ultrasound probe.

20. The method of claim 15, further comprising, after the connecting of the at least one wireless ultrasound probe with the ultrasound diagnosis apparatus, receiving, from the at least one wireless ultrasound probe, status information including at least one of identification information, a wireless communication frequency, a connection type, an executable application, a wireless communication method, battery charging information, a remaining battery capacity, a remaining usability time, and a communication status with respect to each of the at least one wireless ultrasound probe.

21. The method of claim 15, wherein the connecting of the at least one wireless ultrasound probe with the ultrasound diagnosis apparatus comprises connecting with the at least one wireless ultrasound probe by using at least one of wireless communication methods comprising a Wireless Local Area Network (WLAN), wireless fidelity (Wi-Fi), Bluetooth, Zigbee, Wi-Fi Direct (WFD), Infrared Data Association (IrDA), Bluetooth Low Energy (BLE), Near Field Communication (NFC), Wireless Broadband Internet (WiBro), World Interoperability for Microwave Access (WiMAX), Shared Wireless Access Protocol (SWAP), Wireless Gigabit Alliance (WiGig), and radio frequency (RF) communication.

22. The method of claim 15, wherein the connecting of the at least one wireless ultrasound probe with the ultrasound diagnosis apparatus comprises simultaneously pairing the ultrasound diagnosis apparatus with the at least one wireless ultrasound probe.

23. The method of claim 15, wherein the connecting of the at least one wireless ultrasound probe with the ultrasound diagnosis apparatus further comprises checking a status of wireless connection between the ultrasound diagnosis apparatus and the at least one wireless ultrasound probe at preset time intervals.

24. A method of operating an ultrasound diagnosis apparatus comprising a plurality of wireless ultrasound probes, the method comprising:
connecting the ultrasound diagnosis apparatus with each of the plurality of wireless ultrasound probes by using a wireless communication method;
detecting a wireless ultrasound probe being selected by a user, from among the plurality of wireless ultrasound probes;
transmitting an activation signal to the detected wireless ultrasound probe; and transmitting, to the detected wireless ultrasound probe, a beamforming control signal for controlling a beamformer included in the wireless ultrasound probe detected as being selected.

25. The method of claim 24, wherein the connecting of the plurality of wireless ultrasound probes with the ultrasound diagnosis apparatus comprises transmitting and receiving a pairing signal to and from each of the plurality of wireless ultrasound probes by using a wireless communication method.

26. The method of claim 24, further comprising, after the connecting of the plurality of wireless ultrasound probes with the ultrasound diagnosis apparatus, receiving, from the plurality of wireless ultrasound probes, status information including at least one of identification information, a wireless communication frequency, a connection type, an executable application, a wireless communication method, battery charging information, a remaining battery capacity, a remaining usability time, and a communication status with respect to each of the plurality of wireless ultrasound probes.

27. The method of claim 24, wherein the connecting of the plurality of wireless ultrasound probes with the ultrasound diagnosis apparatus comprises simultaneously pairing the ultrasound diagnosis apparatus with the at least one wireless ultrasound probe.

28. A computer-readable recording medium having recorded thereon a program for executing the method of claim 15 on a computer.

* * * * *